US 6,855,813 B2

(12) United States Patent
Rengaraju

(10) Patent No.: US 6,855,813 B2
(45) Date of Patent: Feb. 15, 2005

(54) PROCESS FOR THE PREPARATION OF AZITHROMYCIN MONOHYDRATE

(75) Inventor: Srinivasan Rengaraju, Vadodara (IN)

(73) Assignee: Alembic Limited, Vadodara (IN)

( * ) Notice: Subject to any disclaimer, the term of this patent is extended or adjusted under 35 U.S.C. 154(b) by 9 days.

(21) Appl. No.: 10/197,902

(22) Filed: Jul. 19, 2002

(65) Prior Publication Data

US 2004/0014952 A1 Jan. 22, 2004

(51) Int. Cl.$^7$ ............................................... C07H 1/00
(52) U.S. Cl. ................................... 536/7.4; 536/18.5
(58) Field of Search ................. 536/7.4, 18.5, 536/127

(56) References Cited

U.S. PATENT DOCUMENTS 6,420,537 B1 * 7/2002 Bosch et al. ................ 536/7.4

FOREIGN PATENT DOCUMENTS

| WO | WO 01/00640 A1 | 1/2001 |
| WO | WO 02 42315 A2 | 5/2002 |

* cited by examiner

Primary Examiner—Elli Peselev
(74) Attorney, Agent, or Firm—Banner & Witcoff, Ltd.

(57) ABSTRACT

The invention relates to a process for making Azithromycin crystals using a number of process steps that avoids the use of cumbersome and/or inefficient extraction and/or isolation procedures.

12 Claims, 2 Drawing Sheets

FIG. 1: IR SPECTRUM (KBr PALLET)

PROCESS FOR THE PREPARATION OF AZITHROMYCIN MONOHYDRATE

BACKGROUND OF THE INVENTION

1. Field of the Invention

The invention relates to an improved process for the preparation of Azithromycin monohydrate. More particularly, the invention is directed to a more simplified process for the preparation of Azithromycin monohydrate that circumvents the need to use cumbersome and/or inefficient extraction and/or isolation procedures.

2. Description of the Related Art

Azithromycin (Formula (1)) (USAN generic name for 9-Deoxo-9a-aza-9a-methyl-9a-homo-erythromycin A) is a 15 membered ring macrolide belonging to a new class of antibiotics termed "Azalides", due to the incorporation of a nitrogen atom in the macrocyclic ring:

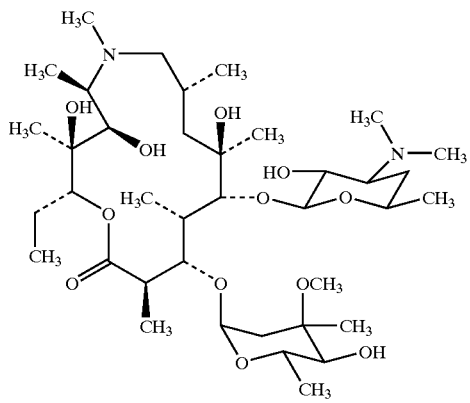

11-(4-Dimethylamino-3-hydroxy-6-methyl-tetrahydro-pyran-2-yloxy)-2-ethyl-3,4,10-trihydroxy-13-(5-hydroxy-4-methoxy-4,6-dimethyl-tetrahydro-pyran-2-yloxy)-3,5,6,8, 10,12,1 4-heptamethyl-1-oxa-6-aza-cyclopentadecan-15-one (Formula (1)) Azithromycin is derived from the 14-membered macrolide antibiotic erythromycin A and shows significant improvement in its activity against gram—Ve organisms compared to erythromycin A (C. J. Dunn and L. B. Barradell Azithromycin: A Review of its Pharmacological properties and use as a 3-day therapy in respiratory tract infections, Drug, 1996, March, 51(3)483-505). The numbering scheme for Azithromycin is indicated in Formula (1) below (which is equivalent to the same Formula (1) depicted above):

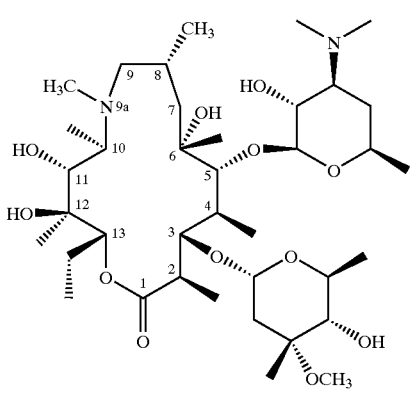

Azithromycin was first discovered by G. Kobrehel and S. Djokic (Belgium Patent No. 892357; related U.S. Pat. No. 4,517,359; S. Djokic et al. J. CHEM. RESEARCH (S), 1988, 132 and idem miniprint, 1988, 1239). U.S. Pat. No. 4,517,359 describes reductive methylation of 11-aza-10-deoxo-10-dihydro erythromycin A (presently called 9-Deoxo-9a-aza-9a-homoerythromycin A) performed with an excess of formaldehyde and formic acid in a halogenated hydrocarbon, e.g., chloroform or carbon tetrachloride. In the procedure described in U.S. Pat. No. 4,517,359,the isolation of Azithromycin involves extraction of the aqueous layer with a halogenated hydrocarbon solvent followed by evaporation of the solvent. The disadvantages of this process are that (i) a halogenated hydrocarbon is used which is environmentally unsafe and (ii) the isolation of azithromycin involves several cumbersome and/or inefficient extraction and solvent evaporation steps.

It is, therefore, an object of this invention is to provide an improved process for preparation of Azithromycin monohydrate, in which the reductive methylation of 9-Deoxo-9a-aza-9a-homoerythromycin A is carried out in a non-halogenated solvent (for example, acetonitrile) and Azithromycin monohydrate crystals are precipitated directly from the reaction mixture without the involvement of cumbersome extraction and/or concentration steps as are described above in relation to U.S. Pat. No. 4,517,359.

Other objects of the invention will be apparent to those of ordinary skill in the art based on the disclosure of this application.

SUMMARY OF THE INVENTION

Figure 1:
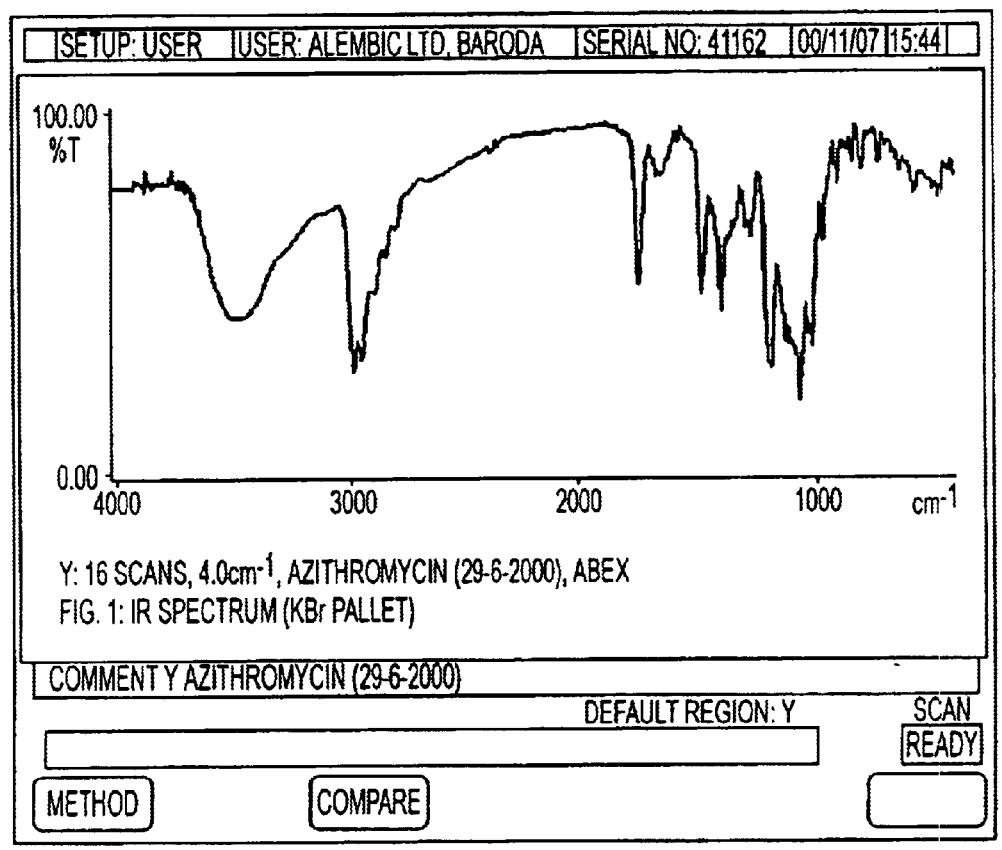
FIG. 1 is an Infrared Spectrum of a sample of Azithromycin monohydrate crystals made according to Example 1.

These and other object(s) of the invention may be accomplished according to one or more of the exemplary embodiments noted below. According to one embodiment of the present invention, the process for making Azithromycin monohydrate crystals comprises the steps of:

(a) dissolving 9-Deoxo-9a-aza-9a-homoerythromycin A in a non-halogenated, water miscible, and non-aqueous solvent to form a solution;

(b) adding formic acid and formaldehyde to the solution;

(c) refluxing the solution to form a reaction mixture;

(d) adjusting the pH of the reaction mixture from about 10 to about 11;

(e) optionally filtering the pH adjusted reaction mixture of step (d); and (f) adding water to the reaction mixture to precipitate the Azithromycin monohydrate crystals.

According to another embodiment of the present invention, the process for making Azithromycin monohydrate crystals comprises the above noted steps (a)–(f) except that in step (a) the non-halogenated, water-miscible, non-aqueous solvent is acetonitrile, N,N-dimethylformamide, N,N-dimethylacetamide, acetone, or iso-propanol.

Preferably, in any of the embodiments described herein, the Azithromycin monohydrate crystals may be dried at a temperature of about 50° C. under vacuum to attain a moisture content of about 4 to 6% w/w. However, other drying temperature and pressure combinations may be used in conjunction with the present invention as described herein to attain a moisture content from about 4 to about 6% w/w of the Azithromycin crystals formed.

DETAILED DESCRIPTION OF THE PREFERRED EMBODIMENTS

According to a preferred embodiment of this invention, an improved process for preparation of Azithromycin monohydrate crystals comprises of the following steps.

(a) dissolving 9-Deoxo-9a-aza-9a-homoerythromycin A in acetonitrile to form a solution;

(b) adding formic acid followed by adding formaldehyde to said solution;

(c) refluxing said solution to form a reaction mixture;

(d) adjusting the pH of said reaction mixture to about 10 to about 11 by using sodium hydroxide;

(e) optionally filtering said reaction mixture to remove any particles;

(f) adding water to the optionally filtered solution to precipitate Azithromycin monohydrate crystals;

(g) filtering said azithromycin monohydrate crystals; and (h) drying said crystals under vacuum at 50° C. to attain a moisture content of about 4 to about 6% by weight based on a total weight of said crystals.

Preferably, in any of the embodiments described herein, the Azithromycin monohydrate crystals can be dried either at ambient temperature and pressure or at various other drying conditions which are encompassed within the scope of the invention including, but not limited to, any temperature and pressure drying combination that provides dried crystals having a moisture content of about 4 to about 6% w/w without (or without substantially) diminishing the yield and/or purity of the precipitated crystals. Of course, variations of the drying temperature and pressure combinations are within the scope of the present invention as will be readily recognized by one of ordinary skill in the field of this invention.

In the process of the present invention described above, the acetonitrile solvent described in step (a) can be replaced by any other equivalent solvent such as N,N-dimethylformamide, N,N-dimethylacetamide, acetone or, iso-propanol. In the process of the present invention, the pH of the reaction mixture recited in step (d) can be adjusted, preferably with alkali, such as, sodium hydroxide, potassium hydroxide, ammonium hydroxide or combinations thereof. In step (f) of the present inventive process, water is added to the pH adjusted reaction mixture to precipitate the Azithromycin monohydrate crystals.

According to another embodiment, the process for making Azithromycin monohydrate comprises the steps of:

(a) dissolving 9-Deoxo-9a-aza-9a-homoerythromycin A in acetonitrile to form a solution;

(b) adding formic acid followed by adding formaldehyde to said solution;

(c) refluxing said solution to form a reaction mixture;

(d) adjusting the pH of said reaction mixture from about 10 to about 11 with NaOH;

(e) optionally filtering the pH adjusted reaction mixture of step (d);

(f) adding water to said reaction mixture to precipitate Azithromycin monohydrate crystals (g) filtering said precipitated crystals; and (h) drying said crystals.

The process of the invention will now be described with reference to the following example which is only illustrative and should in no way be interpreted so as to limit the scope of the present invention.

EXAMPLE

Preparation of Azithromycin Monohydrate

Figure 2:
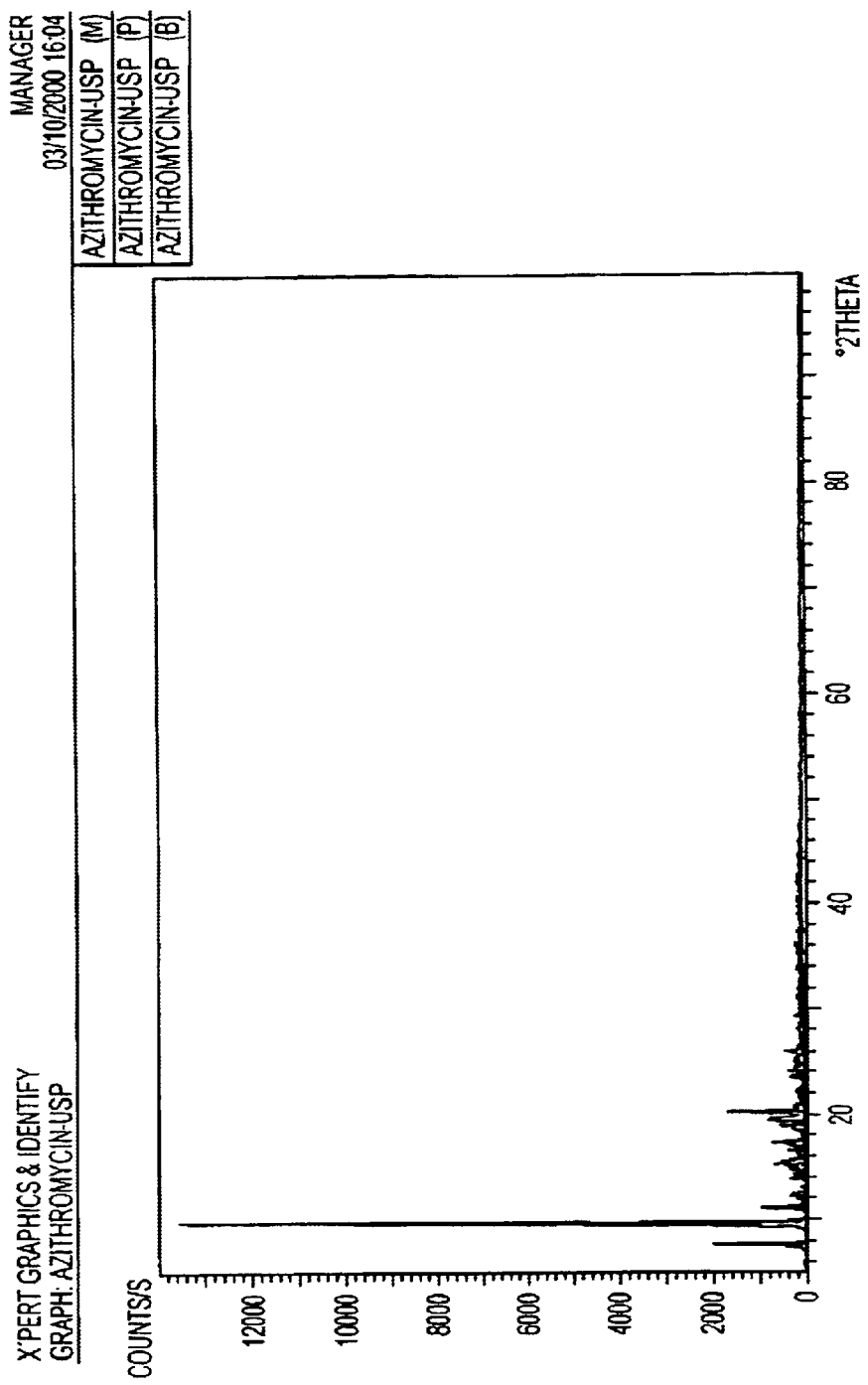
FIG. 2 is an X-ray diffraction of a sample of Azithromycin monohydrate crystals made according to Example 1.

9-Deoxo-9a-aza-9a-homoerythromycin A (73.5 g —0.1 mole) was dissolved in 250 ml acetonitrile. To this solution, formic acid (19 ml, 0.5 mole) followed by formaldehyde (37%, 20 ml, 0.25 mole) were added and refluxed for 24 hours. The pH of the reaction mixture was adjusted with alkali (NaOH solution) to 10.5 and filtered to remove particles. To the filtered acetonitrile solution, an equal volume of water was added to precipitate Azithromycin monohydrate as cube shaped crystals. The crystals were filtered and dried under vacuum at 50° C. to give 65 g of Azithromycin monohydrate having water content of 5% (water content measured by the Karl Fischer titration method). This sample of Azithromycin monohydrate crystals has a characteristic solid state (KBr pellet) IR spectrum (FIG. 1) and a characteristic X-ray diffraction pattern (FIG. 2).

In the process described above reductive methylation is carried out in acetonitrile (solvent) and Azithromycin monohydrate crystals are directly precipitated from the reaction mixture without the need for conducting any extraction procedure.

All patent, patent applications, articles, publications, textbooks and any other references cited in this application are incorporated herein by reference in their entirety for all purposes.

I claim:

1. A process for making Azithromycin monohydrate crystals, said process comprising the steps of:

(a) dissolving 9-Deoxo-9a-aza-9a-homoerythromycin A in acetonitrile, to form a solution;

(b) adding formic acid and formaldehyde to said solution;

(c) refluxing said solution to form a reaction mixture;

(d) adjusting the pH of said reaction mixture from about 10 to about 11 with alkaline solution;

(e) optionally filtering the pH adjusted reaction mixture of step (d);

(f) adding water to said reaction mixture to precipitate said Azithromycin monohydrate crystals directly from said reaction mixture;

(g) filtering out said Azithromycin monohydrate crystals precipitated in said step (f); and (h) drying said Azithromycin monohydrate crystals, wherein said process is conducted without an extraction step.

2. The process of claim 1, wherein said drying step (h) comprises drying said Azithromycin monohydrate crystals at 50° C. under vacuum to attain a moisture content from about 4% to about 6% based on a total weight of said crystals.

3. The process of claim 1, wherein said alkaline solution is selected from the group consisting of sodium hydroxide solution, potassium hydroxide solution, and ammonium hydroxide solution.

4. The process of claim 3, wherein said alkaline solution is sodium hydroxide solution.

5. The process of claim 1, wherein said optional step (e) is conducted.

6. The process of claim 1, wherein said refluxing step (c) is conducted for 24 hours in acetonitrile.

7. The process of claim 1, wherein said drying step is conducted at a temperature and pressure sufficient to substantially remove said water and said acetonitrile from said crystals to yield substantially dry crystals of Azithromycin monohydrate having a moisture content from about 4 to about 6% by weight based on a total weight of said crystals.

8. A process for making Azithromycin monohydrate crystals, said process comprising the steps of:
  (a) dissolving 9-Deoxo-9a-aza-9a-homoerythromycin A in acetonitrile to form a solution;
  (b) adding formic acid and formaldehyde to said solution;
  (c) refluxing said solution to form a reaction mixture;
  (d) adjusting the pH of said reaction mixture from about 10 about 11 with alkaline solution;
  (e) optionally filtering the pH adjusted reaction mixture of step (d); and
  (f) adding water to said reaction mixture to precipitate said Azithromycin monohydrate crystals directly from said reaction mixture, wherein said process is conducted without an extraction step.

9. The process of claim 8, further comprising the step of:
  (g) filtering out said Azithromycin monohydrate crystals precipitated from step (f).

10. The process of claim 9, further comprising the step of:
  (h) drying said Azithromycin monohydrate crystals to attain a moisture content from about 4% to about 6% based on a total weight of said crystals.

11. The process of claim 1, wherein, in said step (b), said formaldehyde is added to said solution after adding said formic acid.

12. A process for making Azithromycin monohydrate, said process comprising the steps of:
  (a) reductively methylating, in a reaction mixture, 9-Deoxo-9a-aza-9a-homoerythromycin A dissolved in acetonitrile, and
  (b) adding water to said reaction mixture to precipitate said Azithromycin monohydrate directly from said reaction mixture, wherein said process is conducted without an extraction step.

* * * * *

UNITED STATES PATENT AND TRADEMARK OFFICE
CERTIFICATE OF CORRECTION

PATENT NO. : 6,855,813 B2
DATED : February 15, 2005
INVENTOR(S) : Srinivasan Rengaraju It is certified that error appears in the above-identified patent and that said Letters Patent is hereby corrected as shown below:

Column 5,
Line 28, replace "10 about 11" with -- 10 to about 11 --.

Signed and Sealed this

Twenty-seventh Day of December, 2005

JON W. DUDAS
*Director of the United States Patent and Trademark Office*